(12) United States Patent
Fallis et al.

(10) Patent No.: US 9,448,212 B2
(45) Date of Patent: Sep. 20, 2016

(54) METHOD FOR THE DETECTION OF SULPHUR CONTAINING PHOSPHORYLATING AGENTS

(75) Inventors: Ian Fallis, South Glamorgan (GB); Ian Morgan, South Glamorgan (GB)

(73) Assignee: UNIVERSITY COLLEGE CARDIFF CONSULTANTS LIMITED, Cardiff (GB)

( * ) Notice: Subject to any disclaimer, the term of this patent is extended or adjusted under 35 U.S.C. 154(b) by 100 days.

(21) Appl. No.: 13/879,859

(22) PCT Filed: Oct. 17, 2011

(86) PCT No.: PCT/GB2011/052003
§ 371 (c)(1),
(2), (4) Date: Apr. 17, 2013

(87) PCT Pub. No.: WO2012/052746
PCT Pub. Date: Apr. 26, 2012

(65) Prior Publication Data
US 2013/0224873 A1 Aug. 29, 2013

(30) Foreign Application Priority Data
Oct. 18, 2010 (GB) .................................. 1017547.9

(51) Int. Cl.
| | | |
|---|---|---|
| *G01N 31/22* | (2006.01) | |
| *C07D 257/04* | (2006.01) | |
| *C07D 417/04* | (2006.01) | |
| *C07D 417/14* | (2006.01) | |
| *C07D 487/04* | (2006.01) | |

(52) U.S. Cl.
CPC ............. *G01N 31/22* (2013.01); *C07D 257/04* (2013.01); *C07D 417/04* (2013.01); *C07D 417/14* (2013.01); *C07D 487/04* (2013.01); *Y10T 436/18* (2015.01)

(58) Field of Classification Search
CPC .. G01N 31/22; C07D 257/04; C07D 417/04; C07D 487/04; C07D 417/14
USPC ........... 436/104, 119–121; 422/400; 548/250
See application file for complete search history.

(56) References Cited

U.S. PATENT DOCUMENTS

| | | | | |
|---|---|---|---|---|
| 3,887,372 A | * | 6/1975 | Bailey ............................ | 430/147 |
| 3,887,374 A | * | 6/1975 | Brongo et al. ................ | 430/147 |
| 4,233,400 A | | 11/1980 | Fujiwara et al. | |
| 4,727,008 A | * | 2/1988 | Lelental et al. ............... | 430/292 |
| 4,837,331 A | * | 6/1989 | Yamanishi et al. ........... | 548/146 |
| 4,946,769 A | * | 8/1990 | Arai et al. ..................... | 430/539 |
| 4,978,613 A | * | 12/1990 | Bieniarz et al. ................ | 435/18 |
| 7,507,585 B2 | * | 3/2009 | Whalen ........................ | 436/120 |
| 2005/0214885 A1 | * | 9/2005 | Yamakoshi et al. ............ | 435/15 |
| 2006/0154376 A1 | * | 7/2006 | Whalen ........................ | 436/120 |
| 2012/0077278 A1 | * | 3/2012 | Roelant et al. ............... | 436/119 |

FOREIGN PATENT DOCUMENTS

| | | |
|---|---|---|
| EP | 0 127 179 | 5/1984 |
| EP | 0 476 456 | 9/1991 |
| EP | 1 002 874 | 5/2000 |
| JP | 58-207042 | 12/1983 |
| JP | 64-68660 | 3/1989 |
| WO | 90/12318 | * 10/1990 |
| WO | 97/38985 | 10/1997 |
| WO | 2006/076619 | 7/2006 |
| WO | 2012/052746 | 4/2012 |

OTHER PUBLICATIONS

Anliker R. et al, Journal of Agriculture and food Chemistry 1963, 11, 291-293.*
Liu, W. et al, Biochemistry and Molecular Biology International 1997, 42, 277-283.*
Xu, Y.-J. ewt al, Clinica Chimica Acta 2002, 325, 127-131.*
Bates, J. A. R., Analyst 1965, 90, 453-466.*
Intellectual Property Office (Great Britain); Great Britain Application No. 1017547.9; Search Report; Jan. 12, 2011.
Kolesnikova, A. M. et al; Photometric Determination of Sulphur With Triphenyltetrazolium Derivatives; Zavodskaya Laboratoriya, vol. 51, No. 11, Nov. 1985, pp. 1-6.
Alexandrov A., et al; Photometrische Bestimmung Von Sulfid Mit Jodnitroltetrazoliumchlorid; Fresenius Z. Anal. Chem. 288, pp. 187-190, 1977 (English Abstract).
Deguchi, Y.; A Histochemical Method for Demonstrating Protein-Bound Sulfhydryl and Disulfide Groups With Nitro Blue Tetrazolium; Department of Oral Surgery, Osaka University Dental School, J Histochem Cytochem. Apr. 1964; 12:261-5.
Gershman, M., et al; Use of a Tetrazolium Salt for an Easily Discernible Sulfide-Motility Reaction; Department of Animal Pathology, University of Maine, J Bacteriol. Nov. 1959; 78(5): 739-740.
Hausser, I., et al.; Uber Die Rot Gelb Umlagerung Von Formazanen Im Licht; Grenzfragen Von Mesomerie Und Isomerie; Kauser-Wilhelm-Institut for Medizinische Forschung Heidelber, Aug. 1, 1949 (English abstract), Chem. Ber, 1949, vol. 82, pp. 195-199.
Hausser, I., et al; Ein Blau Fluorescierendes Bestrahlungsprodukt Von Triphenyl-Tetrazolium-Chlorid.; Kauser-Wilhelm-Institut for Medizinische Forschung Heidelberg, Dec. 10, 1948 (English abstract), Chem. Ber. 1949, vol. 82, pp. 515-527.
Knapp, R., et al; Palladium-Catalyzed Arylation of Ferrocene Derivatives: A Convenient High Yield Route to 1, 1'-Bis(Halophenyl)Ferrocenes; Journal of Organometallic Chemistry, 452, 235-240, 1993.
Muralikkrishna, U., et al; 2, 3, 5-Triphenyltetrazolium Chloride as a New Reagent for the Detection of Sulphide and Some Organic Thiocompounds; Department of Chemistry; Andhra University, Current Science 1974, 43, 706-707.
Nineham, A. W.; The Chemistry of Formazans and Tetrazolium Salts; Research Laboratories, Chem. Rev. 25, 355-483 (1955).
Weiner, S.; The Decomposition Kinetics of 2,3,5-Triphenyl-(2H)-Tetrazolium Hydroxide; University of Wisconsin Extension Center, Wisconsin Academy of Sciences, Arts and Letters;, vol. 46, 1957.

* cited by examiner

*Primary Examiner* — Arlen Soderquist
(74) *Attorney, Agent, or Firm* — Jackson Walker LLP

(57) ABSTRACT

A method is provided for detecting sulphur-containing species (such as thiophosphorous esters, in particular phosphorylating agents), in which a suspected sulphur-containing species is brought into contact with a tetrazolium compound in the presence of base, typically at a pH of at least 8. A device, kit and tetrazolium compounds for use in such a method are also disclosed.

12 Claims, No Drawings

METHOD FOR THE DETECTION OF SULPHUR CONTAINING PHOSPHORYLATING AGENTS

The present invention relates to a method and device for the detection of sulphur containing species, in particular (but not exclusively) potentially dangerous sulphur-containing species, such as phosphothioesters e.g. the cholinesterase inhibitors ('nerve agents') VX and VG.

VX and its variants form a class of highly toxic organo-phosphorous chemical warfare agents. The contact $LD_{50}$ for VX for an adult human is very low [10 mg] and smaller amounts can be incapacitating. Detecting VX and similar compounds can be difficult; VX has a very low vapour pressure and so gas phase detection is often ineffective. Detection by instrument based techniques such as mass spectrometry is time consuming, expensive, requires expert training and is often impractical in the field.

The present invention seeks to mitigate one or more of the problems mentioned above.

In accordance with a first aspect of the present invention, there is provided a compound having structure 1:

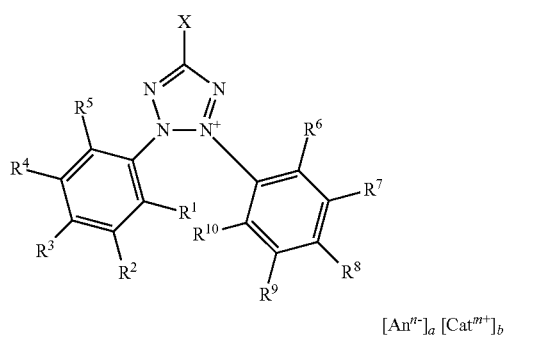

Structure 1

$[An^{n-}]_a [Cat^{m+}]_b$

Wherein $R^1$ to $R^{10}$ are independently selected from the group consisting of H, halogen, $C_{1-12}$ alkyl, $-NO_2$, $-SO_3^-$, $C_{1-12}$ alkoxy and $C_{1-12}$ alkenyl,
or alternatively any two of groups $R^1$ to $R^{10}$ on adjacent carbon atoms are joined to form a ring which may optionally be substituted Provided that one or both of $R^5$ and $R^{10}$ is not H or is joined to form a ring with $R^4$ or $R^9$ respectively,
And if $R^5$ is not H or is joined to form a ring with $R^4$ (but $R^{10}$ is H and is not joined to form a ring with $R^9$), then at least one of $R^1$ and $R^2$ is not H, or $R^1$ and $R^2$ are joined to form a ring;
And if $R^{10}$ is not H or is joined to form a ring with $R^9$ (but $R^5$ is H and is not joined to form a ring with $R^4$), then at least one of $R^6$ and $R^7$ is not H, or $R^6$ and $R^7$ are joined to form a ring;
And if both of $R^5$ and $R^{10}$ are not H or are joined to form a ring with $R^4$ or $R^9$ respectively, then at least one of $R^1$, $R^2$, $R^6$ and $R^7$ is not H, or $R^1$ and $R^2$ are joined to form a ring, or $R^6$ and $R^7$ are joined to form a ring;
X is selected from the group consisting of $-CN$, $-SH$, $-OH$, $-CONH_2$, $-OR^{20}$, $-CO_2R^{20}$, alkyl, aryl, alkenyl, alkyl aryl, aryl alkyl and alkenyl aryl, wherein $R^{20}$ is selected from the group consisting of alkyl, aryl, alkenyl, alkyl aryl, aryl alkyl and alkenyl aryl, and X is optionally substituted;

$An^{n-}$ is a counter anion, which may be absent or present (a being from 0 to 5); and
$Cat^{m+}$ is a counter cation, which may be absent or present (b being from 0 to 5).

Compounds of the first aspect of the present invention have been found to be stable to exposure to UV and visible light and stable to exposure to base, therefore permitting the compounds to be used in the method of the present invention which is described below. Furthermore, the compounds of the first aspect of the present invention may be stable in solution for periods of at least one month at 40° C.

For example, if the tetrazolium core carries a net negative charge (e.g. if two or more of $R^1$ to $R^{10}$ comprise $SO_3^-$), then the compound may be provided with counter cation $Cat^{m+}$.

$R^4$ and $R^5$ may be joined to form a ring which may optionally be substituted.

$R^6$ and $R^7$ may be joined to form a ring which may optionally be substituted.

$R^1$ and $R^2$ may be joined to form a ring which may optionally be substituted.

$R^9$ and $R^{10}$ may be joined to form a ring which may optionally be substituted.

Those skilled in the art will realise that, for example, $R^4$ and $R^5$ may be joined to form a ring which may optionally be substituted, and $R^6$ and $R^7$ may be joined to form a ring which may optionally be substituted.

$R^5$ is optionally selected from the group consisting of halogen, $C_{1-12}$ alkyl, $-NO_2$, $-SO_3^-$, $C_{1-6}$ alkoxy and $C_{1-12}$ alkenyl, and that one or both of $R^1$ and $R^2$ is optionally independently selected from the group consisting of halogen, $C_{1-12}$ alkyl, $-NO_2$, $-SO_3^-$, $C_{1-12}$ alkoxy and $C_{1-12}$ alkenyl or that $R^1$ and $R^2$ are joined to form a ring. One of $R^1$ and $R^2$ is optionally independently selected from the group consisting of halogen, $C_{1-12}$ alkyl, $-NO_2$, $-SO_3^-$, $C_{1-12}$ alkoxy and $C_{1-12}$ alkenyl, and the other of $R^1$ and $R^2$ is optionally H. $R^5$ and one of $R^1$ and $R^2$ are optionally independently selected from the group consisting of halogen and $C_{1-12}$ alkyl.

If $R^5$ is not H, then $R^6$ to $R^{10}$ are optionally independently selected from the group consisting of H, halogen and $C_{1-12}$ alkyl, and optionally that $R^6$ to $R^{10}$ are H.

X is optionally selected from the group consisting of aryl, alkyl aryl, aryl alkyl and alkenyl aryl, and optionally comprises 1-12 carbon atoms. X is optionally aryl alkyl and preferably has structure 2:

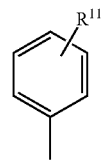

Structure 2 wherein $R^{11}$ is $C_{1-6}$ alkyl, optionally $C_{3-6}$ alkyl, optionally $C_4$ alkyl. $R^{11}$ is optionally located 'para' or 'meta' to the tetrazolium ring.

$An^-$ is optionally selected from the group consisting of $Cl^-$, $F^-$, $Br^-$, $I^-$, $PF_6^-$, $NO_3^-$, $ClO_4^-$, $BF_4^-$, $B(Ar')_4^-$ (where $Ar'$ may include $C_6F_5$, $3,5\text{-}(CF_3)_2C6H_3$, $4\text{-}(CF_3)C_6H_4$) $SO_4^{2-}$, $CF_3SO_3^-$, $C_4F_9SO_3^-$, $F_2HCCF_2F_9SO_3^-$, $AlCl_4^-$, $^-N(SO_2CF_3)_2$, $RSO_3^-$ (where R may include alkyl, aryl, alkyl-aryl, aryl-alkyl, alkyl ether) and $ROSO_3^-$ (where R may include alkyl, aryl, alkyl-aryl, aryl-alkyl, alkyl ether)

If $Cat^{m+}$ is present, then m may typically be 1 or 2. $Cat^{m+}$ may be selected from the group consisting of $Li^+$, $Na^+$, $K^+$, $Rb^+$, $Cs^+$, $Mg^{2+}$, $Ca^{2+}$, $Sr^{2+}$, $Ba^{2+}$, $R_4N^+$ (where R=n-alkyl $C_1$-$C_{12}$ or a mixture and branched versions thereof, benzyl) and $R_4P^+$ (where R=n-alkyl $C_1$-$C_{12}$ or a mixture and branched versions thereof, benzyl, aryl, or a mixture of aryl and alkyl groups).

It is optional that a is 0, 1 or 2. It is optional that b is 0, 1 or 2.

In accordance with a second aspect of the present invention, there is provided a method for the detection of sulphur containing species, the method comprising:

Bringing together a tetrazolium reagent, a suspected sulphur-containing species and one of:

A base in alkaline conditions or a nucleophilic base in non-aqueous conditions.

The method of the present invention provides an inexpensive, rapid and practical method for determining the presence of a sulphur-containing species.

The tetrazolium reagent, suspected sulphur-containing species and a nucleophilic base may be brought together in non-aqueous conditions, for example, using hydrazine or hydroperoxide anions as a nucleophilic base.

The term "sulphur-containing species" includes, but is not limited to, sulphur-containing compounds. If the tetrazolium reagent, suspected sulphur-containing species and base are brought together in alkaline conditions, the pH may be at least 8, optionally at least 9, optionally at least 10, optionally at least 11, optionally at least 12, and optionally up to 13.5, and optionally up to 14. The pH may typically be measured using a pH meter or pH probe.

References below to "base" refer to both the base used in alkaline (i.e. aqueous) conditions and the nucleophilic base used in non-aqueous conditions, unless the context of a statement requires otherwise.

The tetrazolium reagent is optionally substantially stable to exposure to UV light and substantially stable in the presence of base. "Substantially stable in the presence of base" may indicate that the reagent is stable in the presence of base (but in the absence of other species with which the tetrazolium reagent may react), at a pH of 11, optionally at a pH of 12 and optionally at a pH of 13.

"Substantially stable to exposure to UV light" may indicate that the reagent does not form a significant proportion of photo-derived species when a solution (10 mM) of the compound is exposed to UV light having a wavelength of 365 nm from a lamp of nominal 6 W. power for 1 hour. Mass spectrometry may be used to determine whether a tetrazolium reagent has reacted when exposed to UV light.

The tetrazolium reagent is optionally substantially stable to exposure to UV light in the presence of base. The tetrazolium reagent is optionally stable in both a solution and in solid form.

The base and light stability of the tetrazolium reagent in solution was established by the addition of a hydroxide ion source (e.g. sodium, hydroxide, potassium hydroxide or tetra n-butyl ammonium hydroxide (TBAOH)) or an amine (e.g. ammonia, triethanolamine, diethanolamine, triethylamine (TEA), pyridine, imidazole or N-methylimidazole) to solution of the tetrazolium salt (5 mM) in water (for $An^-$=$Cl^-$, $Br^-$, $NO_3^-$), in a 1:1 water:solvent (e.g. ethoxy ethanol, butoxyethanol) mixture or dichloromethane (for other $An^-$ and $An^-$ salts). In tests of base stability with hydroxide ion sources the pH was set at 12-13 by the addition of small aliquots of either 10 M NaOH, 10 M KOH or 40 wt. % TBAOH. In tests of base stability with amines 10 wt. % of amine (10% w/v for 28.0-30.0% aqueous ammonia) was used in making up the stock tetrazolium salt solutions. The tetrazolium reagents were deemed stable if there was no discernable colour change to the naked eye after stirring under an aerobic atmosphere in a well lit room for a period of 24 hours.

The base and light stability of a tetrazolium reagent in a solid state may be tested for by absorbing a solution (5 mM) of the tetrazolium reagent on a substrate (e.g. filter paper) and then drying. The paper may then be treated by spraying with an aqueous solution of base (e.g. hydroxide sources, amines or heterocyclic bases) and then drying. The tetrazolium reagents so treated were deemed stable if there was no discernable colour change to the naked eye storage under an aerobic atmosphere in a well lit room for a period of 24 hours.

The tetrazolium reagent may be substantially stable to exposure to UV light and visible light.

The tetrazolium reagent may be stable in solution for a period of at least one month at 40° C.

Whilst not wishing to be bound by theory, it is believed that the method of the present invention comprises the formation of a formazan species, optionally in the form of a formazan anion. It is believed that in the case of a thioester a thiolate ion is formed from the suspected sulphur-containing species. The thiolate ion may then react with the tetrazolium reagent to form a disulphide and a formazan compound which at high pH takes the form of a formazan anion.

The sulphur-containing species which may be detected using the method of the present invention comprise organic species (e.g. VX) and inorganic species (e.g. hydrogen sulphide).

The species which may be detected may comprise a sulphur moiety bonded with a single bond to an adjacent moiety (such as carbon or phosphorus).

The species which may be detected using the method of the present invention include thiols, thioethers, thioesters, hydrogen sulphide and phosphorous thioesters.

The species which may be detected may comprise phosphorylating agents, such as VX or certain organophosphorous pesticides. Examples of organophosphorus pesticides and related substances include Omethoate, Amifostine, Demeton-S-methyl, Vamidothion, Iprobenfos, Malaoxon, Azamethiphos and Profenofos.

Reaction of the tetrazolium reagent and a sulphur-containing species may lead to the formation of a coloured species, formation of a coloured species being indicative of the presence of the sulphur-containing species. The method of the present invention may therefore comprise sensing for the presence of colouration. The colouration may be associated with the formation of a formazan species, such as a formazan anion. The colouration is typically red.

The method may comprise sensing the speed of formation of colouration. Sensing the speed of formation may be performed qualitatively (for example, by observation with the human eye) or quantitatively (for example, by measurement using a spectrometer or the like). Whilst not wishing to be bound by theory, the applicant believes that the speed of the colour change may be related to the nature of the analyte in question. For thioesters and phosphorus thioester analytes the rate determining step is believed to be the scission of the S—C and S—P bonds respectively. Hence for given quantities of analyte, thiols, thiolates, thioacids and sulfides react almost instantaneously whilst thioesters and phosphorus thioester analytes react rapidly with the colour increasing over a period of seconds to minutes. Thus the applicant believes that the rate of colour change is indicative of the nature of the analyte.

The method may comprise sensing the intensity of colouration, the intensity of colouration being indicative of the concentration of the sulphur-containing species. Sensing the intensity of colouration may be performed qualitatively (for example, by observation with the human eye) or quantitatively (for example, by measurement using a spectrometer or the like).

The method may comprise bringing together the suspected sulphur-containing species, the base and tetrazolium reagent.

The method may alternatively comprise bringing together the suspected sulphur-containing species and the tetrazolium reagent, and subsequently bringing together the base with the suspected sulphur-containing species and the tetrazolium reagent. Those skilled in the art will realise that the bringing together of the base with the suspected sulphur-containing species and the tetrazolium reagent may comprise moving the tetrazolium reagent and suspected sulphur-containing species into contact with the base or moving the base into contact with the tetrazolium reagent and the suspected sulphur-containing species.

The method may alternatively comprise bringing together the suspected sulphur-containing species and the base and subsequently bringing together the tetrazolium reagant with the suspected sulphur-containing species and the base. Those skilled in the art will realise that the bringing together of the tetrazolium reagent with the suspected sulphur-containing species and the base may comprise moving the tetrazolium reagent into contact with the suspected sulphur-containing species and base or moving the suspected sulphur-containing species and base into contact with the tetrazolium reagent.

The tetrazolium reagent optionally has a structure in accordance with formula 3:

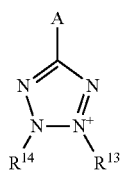

Structure 3

Where $R^{13}$ and $R^{14}$ are bulky substituents,
A is a bulky substituent or is selected from the group consisting of —CN, —SH, —OH, —CONH$_2$, —OR$^{20}$, —CO$_2$R$^{20}$, alkyl, aryl, alkenyl, alkyl aryl, aryl alkyl and alkenyl aryl, wherein $R^{20}$ is selected from the group consisting of alkyl, aryl, alkenyl, alkyl aryl, aryl alkyl and alkenyl aryl, and A is optionally substituted.

The reagent of structure 3 may be associated with one or more counter anion, $An^{n-}$, which may be absent or present, and one or more counter cations, $Cat^{m+}$, which may be absent or present.

$R^{12}$, $R^{13}$ and $R^{14}$ may be the same or different (and are optionally different) and each may be an optionally substituted hydrocarbon moiety having at least four (and optionally at least six) carbon atoms.

Each of $R^{12}$, $R^{13}$ and $R^{14}$ optionally comprises an aromatic moiety or a heterocyclic moiety which may be substituted in one or more positions. Heterocyclic moieties include pyridinyl, thiazolyl, oxazolyl, imidazolyl, quinolinyl, isoquinolinyl, benzothiazolyl and benzoxazolyl. The aromatic moiety optionally comprises an aryl moiety. Each of $R^{12}$, $R^{13}$ and $R^{14}$ optionally comprises an optionally-substituted phenyl moiety.

$R^{12}$ optionally comprises a phenyl moiety substituted with one or more alkyl groups, optionally $C_{1-6}$ alkyl groups. $R^{12}$ optionally comprises a phenyl moiety substituted with one $C_{1-12}$ alkyl group, optionally a $C_{4-6}$ alkyl group, optionally a $C_4$ alkyl group.

$R^{14}$ optionally comprises a phenyl moiety substituted with one or more substituents, each substituent optionally being selected from the group consisting of halogen, $C_{1-12}$ alkyl, —NO$_2$, —SO$_3^-$, $C_{1-12}$ alkoxy and $C_{1-12}$ alkenyl. The phenyl moiety is optionally provided with at least two or three substituents, only two or three substituents (and optionally only two) substituents. One substituent is optionally located ortho to the tetrazole ring, and another substituent is optionally located either at the second position ortho to the tetrazole ring, or at the position meta to the tetrazole ring (and adjacent to the second position ortho to the tetrazole ring).

$R^{13}$ may comprise a phenyl moiety substituted with one or more substituents, each substituent optionally being selected from the group consisting of halogen, $C_{1-12}$ alkyl, —NO$_2$, —SO$_3^-$, $C_{1-12}$ alkoxy and $C_{1-12}$ alkenyl. The phenyl moiety may be provided with no or one substituent. If the phenyl moiety is provided with one substituent, the substituent is optionally located ortho to the tetrazole ring.

The tetrazolium compound may have a structure of Structure 1 i.e. may be a tetrazolium compound in accordance with the first aspect of the present invention.

The method may comprise providing a device for detecting the presence of a sulphur-containing species. The device may comprise a substrate provided with the tetrazolium reagent. The method may comprise contacting the substrate with the suspected sulphur-containing species. The substrate may be provided with the tetrazolium reagent by depositing a solution of tetrazolium reagent onto the substrate and then drying.

The substrate may further be provided with base. The substrate may be provided with base by depositing a basic solution onto the substrate and then drying. Alternatively, the substrate may be formed from a basic material (such as a carbonate, a basic resin or an ionic exchange medium).

The substrate may comprise a porous substrate. Such substrates are inexpensive and readily absorb reagents.

The method may comprise providing a kit for detecting the presence of a sulphur-containing species, the kit comprising a substrate optionally provided with the tetrazolium reagent and/or base, and, if the substrate is not provided with the tetrazolium reagent or base, then the kits further being provided with one or more of a basic solution, a solution of tetrazolium reagent and a sample collector.

The solution of tetrazolium reagent and basic solution may be provided as one solution.

The basic solution may comprise a 0.001 to 10M solution of hydroxide ions, optionally a 0.05 to 0.5M solution and optionally a 0.05 to 0.2M solution.

The sample collector may be suitable for collecting a liquid sample. The sample collector may comprise a surface for the collection of a sample, the surface being provided by an absorbent material. The sample collector may comprise a chamber for holding a sample and a means for urging a sample into the chamber. The means for urging a sample into the chamber may comprise a means for decreasing the pressure in the chamber prior to sample collection (such as the bulb of a pipette). The sample collector may, for example, comprise a pipette.

In accordance with a third aspect of the present invention, there is provided a device for the detection of sulphur containing species, the device comprising:
a substrate provided with a tetrazolium reagent.

The substrate may be provided with the tetrazolium reagent by depositing a solution of tetrazolium reagent onto the substrate and then drying. The substrate may be absorbent.

The substrate may further be provided with base. The substrate may be provided with base by depositing a basic solution onto the substrate and then drying. Alternatively, the substrate may be formed from a basic material (such as a carbonate or a basic resin).

The tetrazolium reagent may have structure and/or properties as discussed above in relation to the method of the second aspect of the present invention. For example, the tetrazolium reagent may be substantially stable to exposure to UV light and substantially stable in the presence of base. Furthermore, the tetrazolium reagent may have the structure 3 as discussed above in relation to the method of the second aspect of the present invention.

The tetrazolium reagent provided in the device may be the tetrazolium ion described in accordance with the first aspect of the present invention i.e. the ion having structure 1.

The device of the third aspect of the present invention may be used in the method of the second aspect of the present invention.

In accordance with a fourth aspect of the present invention, there is provided a kit for the detection of sulphur containing species, the kit comprising a device in accordance with the third aspect of the present invention and one or both of a basic solution and a sample collector.

The basic solution may comprise a 0.001 to 10M solution of hydroxide ions, optionally a 0.05 to 0.5M solution and optionally a 0.05 to 0.2M solution.

The sample collector may be suitable for collecting a liquid sample. The sample collector may comprise a surface for the collection of a sample, the surface being provided by an absorbent material. The sample collector may comprise a chamber for holding a sample and a means for urging a sample into the chamber. The means for urging a sample into the chamber may comprise a means for decreasing a pressure in the chamber prior to sample collection (such as the bulb of a pipette). The sample collector may, for example, comprise a pipette.

The kit of the fourth aspect of the present invention may be used in the method of the second aspect of the present invention.

The invention will now be described by way of example only. Those skilled in the art will realise that ownership of Many of the substances which can be detected using the method of the present invention is controlled by international law. Furthermore, those skilled in the art will realise that many of the substances which can be detected using the method of the present invention are extremely toxic and suitable precautions should be taken when handling such materials.

The synthesis of several tetrazolium compounds in accordance with the present invention will now be described.
General Method Overview The general method involves the formation of a phenyl hydrazone which is then coupled with a diazonium species to form a formazan. The formazan is then oxidised with lead tetraacetate to form the tetrazolium compounds of the present invention. Except where noted, all reagents were purchased from Sigma-Aldrich and used without further purification. All solvents were purchased from fisher Scientific and used without further purification.

Synthesis of 4-tert butylphenyl phenyl hydrazone

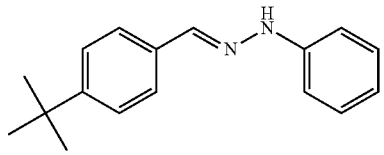 [SMILES: CC(C)(C)c1ccc(/C=N/Nc2ccccc2)cc1]

4-tert butyl benzaldehyde (Tokyo Chemical Industry UK Ltd) (10.0 mmol, 1.60 ml) was dissolved in EtOH (50 ml) and heated to 70° C. with stirring. A solution of phenylhydrazine (1.08 ml, 10.0 mmol) in EtOH (20 ml) was prepared, heated to 70° C. and added in one portion to the aldehyde solution. After several minutes a bright yellow precipitate began to form and the mixture was allowed to stir for a further two hours with heating at 70° C. After the reaction was complete the precipitate was filtered and washed with a small volume of cold ethanol (5 ml) to give a spectroscopically pure sample of the hydrazone (2.20 g, 8.7 mmol, 87%).

$^1$H NMR (250 MHz, CDCl$_3$): δ=1.35 (9H, s of C(CH$_3$)$_3$), 6.85 (1H, m, of C$_6$H$_5$), 7.15 (2H, d, J=1.2, of C$_6$H$_5$), 7.25-7.35 (2H, m, of C$_6$H$_5$), 7.40 (2H, d, J=8.5, of C$_6$H$_4$), 7.60 (2H, d, J=8.4, of C$_6$H$_4$), 7.70 (1H, s, of CHN).

$^{13}$C NMR (62.5 MHz, CDCl$_3$): δ=30.95 of C(CH$_3$), 34.75 of C(CH$_3$), 112.72, 119.94, 125.57, 125.98, 129.29, 132.59, 137.43, 144.83, 151.72 all Ar.

IR (KBr disc, cm$^{-1}$), ν=3298 st, 2960 st, 2897 st, 2863 st, 1597 st, 1494 st, 1357 md, 1248 st, 1128 st, 1111 st, 1065 md, 922 md, 888 md, 756 st, 693 st.

MS (APCI) AP+: M$^+$=252 (100%) exact mass (calc.) 252.3541, exact mass (obs.) 252.3533.
Formazan Preparation—General Method A general method was employed in each case for the formation of the formazans from the 4-tert butyl phenyl phenylhydrazone based on the synthesis of formazans by the coupling to a diazonium salt. The appropriate aniline (2.82 mmol, 1 equiv.) was dissolved in conc. H$_2$SO$_4$ (2 ml) and cooled to 0° C. in an ice bath. Sodium nitrite (0.148 g, 2.82 mmol, 1 equiv.) was dissolved in a H$_2$0 (2 ml), transferred to a dropping funnel and added over 15 minutes to the acidic aniline solution. After the addition was complete the diazonium salt solution was allowed to stir at 0° C. for a further 30 minutes. 4-tert-Butyl phenyl phenylhydrazone (0.710 g, 2.82 mmol, 1 equiv.) was dissolved in pyridine (10 ml) and cooled in a salt-ice bath to −5° C. The diazonium salt solution was the added to the hydrazone solution over 45 minutes. Additional ice was added during the addition and the temperature monitored to keep the solution at −5° C. Additional amounts of pyridine (1 ml) were also added after the 10 minutes of addition at approximately 5 minute intervals to maintain a fluid solution. Once addition of the diazonium salt was complete the resultant red solution was allowed to warm to room temperature and stir overnight. The reaction mixture was extracted with chloroform (50 ml) and washed with water (50 ml), dilute acetic acid (2×50 ml) and water (50 ml) again. The organic layer was dried over MgSO$_4$ and the solvent removed on a rotary evaporator to leave a deep red solid. The product was then recrystallised from hot EtOH (20 ml) to yield fine red crystals.

1-(2,6-dichlorophenyl)-3-(4-tert-butylphenyl)-5-phenyl formazan

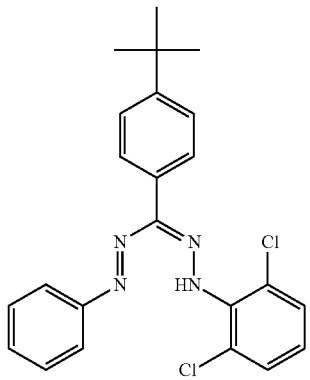

Compound I

This compound was prepared using the above general procedure, using 2,6-dichloroaniline (0.456 g, 2.82 mmol), NaNO$_2$ (0.148 g, 2.82 mmol) and 4-tertiary butyl phenyl hydrazone (0.710 g, 2.82 mmol) to give a red solid (0.475 g, 1.10 mmol, 39%). $^1$H NMR (400 MHz, CDCl$_3$): δ=1.29 (9H, s, of C(CH$_3$)$_3$), 6.96 (1H, t, J=7.6 Hz), 7.29-7.35 (3H, m, 2H of C$_6$Cl$_2$H$_3$, 1H of C$_6$H$_5$), 7.39-7.42 (4H, m, of C$_6$H$_5$), 7.76 (2H, dd, J$_1$=7.2 Hz, J$_2$=1.6 Hz, of C$_6$H$_4$), 8.01 (2H, dd, J$_1$=7.2 Hz, J$_2$=1.6 Hz, of C$_6$H$_4$), 15.00 (1H, s, br, NH); $^{13}$C NMR (100 MHz, CDCl$_3$): δ=31.76 of C(CH$_3$)$_3$, 35.07 of C(CH$_3$)$_3$, 120.72, 125.84, 126.19, 126.96, 129.60, 129.86, 130.18, 134.66, 140.47, 142.94, 149.70 (all of Ar), 151.44 of N=N—C=N—N. IR (KBr disc, cm$^{-1}$), ν=3390 br, st, 2962, 1598 st, 1498 st, 1482 st, 1394 w, 1245 st, 865 md, 840 md. UV/Vis (chloroform): λ$_{max}$ (ε) 297 nm, ε=22,190 cm$^{-1}$ mol$^{-1}$ dm$^3$ λ$_{max}$ (ε) 482 nm, ε=15,380 cm$^{-1}$ mol$^{-1}$ dm$^3$. MS (APCI) AP+: M$^+$=427 (100%) exact mass (calc.) 427.3694, exact mass (obs.) 427.3698.

1-(2,5-dichlorophenyl)-3-(4-tert-butylphenyl)-5-phenyl formazan

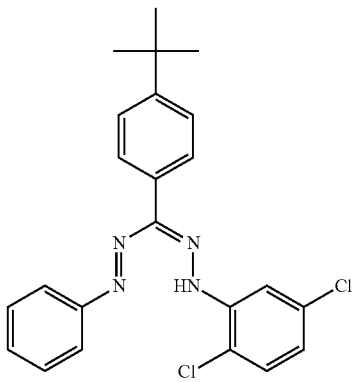

Compound II

Compound III was prepared by the general procedure mentioned above using 2,5-dichloroaniline (0.456 g, 2.82 mmol), NaNO$_2$ (0.148 g, 2.82 mmol) and 4-tertiary butyl phenyl hydrazone (0.710 g, 2.82 mmol) to give a red solid (0.378 g, 0.88 mmol, 31%). $^1$H NMR (400 MHz, CDCl$_3$): δ=1.32 (9H, s, of C(CH$_3$)$_3$), 6.89 (1H, dd, J$_1$=2.4 Hz, J$_2$=5.6 Hz, of C$_6$H$_3$Cl$_2$)), 7.18 (1H, d, J=5.6 Hz, of C$_6$H$_3$Cl$_2$), 7.40-7.45 (5H, m, of C$_6$H$_5$), 7.87 (2H, d, J=8.4 Hz of C$_6$H$_4$), 7.92 (1H, d, J=2.4 Hz, of C$_6$H$_3$Cl$_2$), 7.99 (2H, d, J=8.4 Hz of C$_6$H$_4$), 14.8 ppm (1H, s, br, NH). $^{13}$C NMR (100 MHz, CDCl$_3$): δ=31.37 of C(CH$_3$)$_3$), 34.72 of C(CH$_3$)$_3$, 115.37, 119.71, 122.03, 123.86, 125.46, 126.12, 129.45, 130.27, 131.19, 134.07, 134.23, 142.32, 142.87, 151.37 (all of Ar), 151.42 of N=N—C=N—N. IR (KBr disc, cm$^{-1}$), ν 3364 br, md, 2882 md, 1700 w, 1578 st, 1506 st, 1454 st, 1409 w, 1356 st, 1223 st, 1083 st, 1029 md, 1008 md, 904 md, 865 md. UV/vis (chloroform): λ$_{max1}$ (ε) 487 nm, ε=16,408 cm$^{-1}$ mol$^{-1}$ dm$^3$ λ$_{max2}$ (ε) 293 nm, ε=30,527 cm$^{-1}$ mol$^{-1}$ dm$^3$. MS (APCI) AP+: M$^+$=427 (100%) exact mass (calc.) 427.3694, exact mass (obs.) 427.3682.

1-(2,6-difluorophenyl)-3-(4-tert-butylphenyl)-5-phenyl formazan

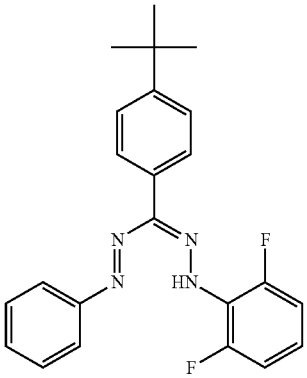

Compound III

Prepared by the general procedure using 2,6-difluoroaniline (Apollo Scientific UK Ltd.) (0.364 g, 2.82 mmol), NaNO$_2$ (0.148 g, 2.82 mmol) and 4-tertiary butyl phenyl hydrazone (0.710 g, 2.82 mmol) to give a red solid (0.452 g, 1.14 mmol, 41%). $^1$H NMR (400 MHz, CDCl$_3$): δ=1.30 (9H, s, of C(CH$_3$)$_3$), 6.92-6.98 (2H, m, of C$_6$F$_2$H$_3$), 7.19-7.25 (1H, m, of C$_6$F$_2$H$_3$), 7.39-7.42 (5H, m, of C$_6$H$_5$), 7.58 (2H, d, J=8.4 Hz, of C$_6$H$_4$), 7.97 (2H, d, J=8.4 Hz, of C$_6$H$_4$). $^{13}$C NMR (100 MHz, CDCl$_3$): δ=30.20 of C(CH$_3$)$_3$, 33.61 of (C(CH$_3$)$_3$, 111.42, 118.34, 124.38, 124.52, 124.64, 124.77, 125.55, 127.19 (all Ar, some peaks coincidental), 128.4 of N=N—C=N—N. IR (KBr disc, cm$^{-1}$), ν 3390 br, md, 2961 md, 1589 md, 1496 st, 1474 st, 1407 md, 1353 md, 1243 st, 1224 md, 1174 md, 1109 w, 1049 st, 1006 md, 839 md. UV/vis (chloroform): λ$_{max1}$ (ε) 297 nm, ε=22,259 cm$^{-1}$ mol$^{-1}$ dm$^3$ λ$_{max2}$ (ε) 490 nm, ε=9,795 cm$^{-1}$ mol$^{-1}$ dm$^3$. MS (APCI) AP+: (M+H$^+$)=394 (100%) exact mass (calc.) 394.4602, exact mass (obs.) 394.4607.

Tetrazolium Formation—General Method

A general method was employed in each case for the formation of simple tetrazoliums based on the oxidation of formazans with lead tetraacetate method reported by Kuhn and Jerchel,[i] The formazan (typically 1.00 mmol) was dissolved in chloroform (30 ml) in a 100 ml round bottomed flask fitted with a stirrer bar. The solution was heated to 60° C. with stirring and lead tetraacetate (Alfa Aesar UK Ltd.) (0.535 g, 1.2 mmol) added in one portion. The solution was stirred with heating for a further two hours by which time the deep red colour had been replaced by a clear pale yellow solution. The solvent was then removed from reaction mixture by means of a rotary evaporator to leave a white solid. To this residue was added 2M HCl (20 ml) and the suspension stirred for another 1 hour. The aqueous solution containing the product as the chloride salt was filtered to remove the insoluble lead chloride formed. A saturated solution of potassium hexafluorophosphate (Alfa Aesar UK Ltd.) was then added and the mixture stirred for a further one hour. This aqueous solution was then extracted with chloroform (3×50 ml), the organic layers seperated, dried over magnesium sulphate, filtered and the solvent removed on a rotary evaporator to leave a pale yellow or white solid.

5-(4-tert-butylphenyl)-2-(2,6 dichlorophenyl)-3 phenyl tetrazolium hexafluorophosphate

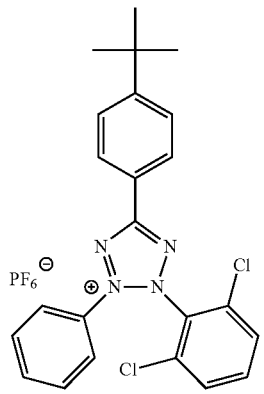

Compound IV

Using the general procedure outlined above with Compound I (0.323 g, 0.76 mmol) as the starting material to give Compound IV as a pale yellow solid (0.251 g, 0.45 mmol, 59%). $^1$H NMR (500 MHz, DMSO): δ=1.35 (9H, s, of C(CH$_3$)$_3$), 7.75-7.80 (4H, m, 2H of C$_6$Cl$_2$H$_3$ and 2H of C$_6$H$_4$), 7.88-7.92 (1H, m, 1H of C$_6$Cl$_2$H$_3$), 7.93-7.96 (5H, m, 5H of C$_6$H$_5$), 8.28 (2H, d, J=8.2 Hz, 2H of C$_6$H$_4$). $^{13}$C NMR (125 MHz, DMSO): δ=30.68 of C($\underline{C}$H$_3$)$_3$, 35.08 of $\underline{C}$(CH$_3$)$_3$, 119.47, 124.97, 126.92, 127.65, 127.81, 130.64, 130.91, 131.76, 132.53, 135.46, 137.84, 157.54 (all Ar), 166.58 of NN$\underline{C}$NN. IR (KBr disc, cm$^{-1}$), ν 3100 br, w, 2964 br, md, 1615 md, 1539 md, 1475 st, 1365 w, 1268 w, 1163 md, 1146 md, 1102 md, 1055 w, 1027 w, 846 st. UV/Vis (chloroform): λ$_{max}$ (ϵ) 264 nm, ϵ=21,940 cm$^{-1}$ mol$^{-1}$ dm$^3$. MS (APCI) AP+: M$^+$=569 (100%) exact mass (calc.) 569.3098, exact mass (obs.) 569.3076.

5-(4-tert-butylphenyl)-2-(2,5-dichlorophenyl)-3-phenyl tetrazolium hexafluorophosphate

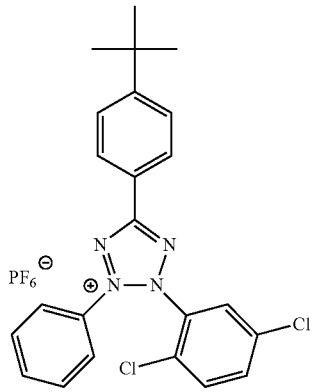

Compound V

Using the general procedure outlined above with Compound II (0.423 g, 1.00 mmol) as the starting material to give Compound V as a pale yellow solid (0.358 g, 0.63 mmol, 63%).

$^1$H NMR (400 MHz, DMSO): δ=1.38 (9H, s, of C(CH$_3$)$_3$), 7.78-7.83 (4H, m, 2H of C$_6$H$_4$ and 2H of C$_6$H$_5$), 7.86-7.92 (3H, m, 1H of C$_6$H$_5$ and 2H of C$_6$H$_4$), 7.98 (1H, d, J=8.4 Hz, 1H of C$_6$Cl$_2$H$_3$) 8.06 (1H, dd, J$_1$=8.4 Hz, J$_2$=2.4 Hz, 1H of C$_6$Cl$_2$H$_3$), 8.28 (2H, d, J=8.0 Hz, of C$_6$H$_4$), 8.36 (1H, d, J=2.4 Hz, 1H of C$_6$Cl$_2$H$_3$);

$^{13}$C NMR (100 MHz, DMSO): δ=30.74 of C($\underline{C}$H$_3$, 35.12 of $\underline{C}$(CH$_3$)$_3$, 119.68, 125.78, 127.04, 127.53, 128.58, 129.67, 130.57, 130.78, 132.22, 133.12, 133.41, 134.92, 136.59, 157.24 (all Ar), 165.44 of NN$\underline{C}$NN;

IR (KBr disc, cm$^{-1}$), ν 2971 w, 2359 w, 1614 st, 1574 md, 1538 st, 1460 st, 1270 md, 1204 md, 1168 w, 1145 md, 995 md, 846 br, st.

UV/vs (chloroform): λ$_{max}$ (ϵ) 263 nm, ϵ=31,380 cm$^{-1}$ mol$^{-1}$ dm$^3$

MS (APCI) AP+: M$^+$=569 (100%) exact mass (calc.) 569.3098, exact mass (obs.) 569.3082.

5-(4-tert-butylphenyl)-2-(2,6-difluorophenyl)-3-phenyl tetrazolium hexafluorophosphate

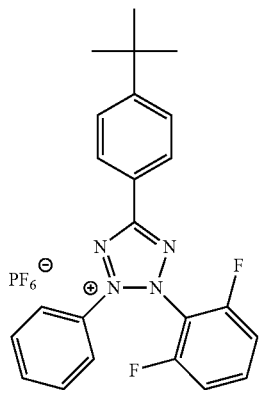

Compound VI

Using the general procedure outlined above with Compound III (0.394 g, 1.00 mmol) as the starting material to give Compound VI as a white solid (0.316 g, 0.59 mmol, 59%). $^1$H NMR (400 MHz, CDCl$_3$): δ=1.33 (9H, s, 9H of C(CH$_3$)$_3$), 7.14-7.22 (1H, m, 1H of C$_6$F$_2$H$_3$), 7.58 (2H, d, J=7.0 Hz, 2H of C$_6$H$_4$), 7.62-7.65 (2H, m, 2H of C$_6$F$_2$H$_3$), 7.68-7.73 (4H, m, 4H of C$_6$H$_5$), 7.78-7.81 (1H, m, C$_6$H$_5$), 8.14 (2H, d, J=7.0 Hz, 2H of C$_6$H$_4$) $^{13}$C NMR (100 MHz, CDCl$_3$): δ=31.04 of C(CH$_3$)$_3$, 35.21 C(CH$_3$)$_3$, 114.30, 119.53, 124.32, 124.60, 124.80, 125.60, 125.97, 126.95, 127.03, 127.85, 128.12, 128.69, 131.16 (all Ar). IR (KBr disc, cm$^{-1}$), ν 2966 md, 1616 st, 1514 st, 1487 st, 1365 st, 1255 md, 1200 md, 1146 md, 1024 md, 999 md, 825 st. UV/Vis (chloroform): λ$_{max}$ (ε) 265 nm, ε=27,361 cm$^{-1}$ mol$^{-1}$ dm$^3$ MS (APCI) AP+: =536 (100%) exact mass (calc.) 536.4006 exact mass (obs.) 536.4023.

Further hexafluorophosphate compounds were synthesised in a manner analogous to that described above and these are now listed:
5-(4-tert-butylphenyl)-2-(2,6 dimethyl)-3 phenyl tetrazolium hexafluorophosphate (Compound VII)
5-phenyl-2-(2,6-dimethyl)-3 phenyl tetrazolium hexafluorophosphate
5-phenyl-2-(2,6-difluorophenyl)-3 phenyl tetrazolium hexafluorophosphate
5-phenyl-2-(2,5-dichlorophenyl)-3 phenyl tetrazolium hexafluorophosphate
5-phenyl-2-(2,6-dichlorophenyl)-3 phenyl tetrazolium hexafluorophosphate Chloride analogues of all of the hexafluorophosphate compounds mentioned above were also synthesised.

The base and UV stability of the tetrazolium compounds mentioned above were examined as now described.

Testing of UV Stability

The salt was dissolved in an appropriate solvent (water for the chloride and dichloromethane for the hexafluorophosphate) to afford 5 mM solutions and a sample introduced into a 1 cm path length quartz cuvette. The cuvette and its contents were exposed to "soft" UV light having a wavelength of 365 nm provided by a standard laboratory 6 W chromatography style lamp for 1 hour. Two solutions of triphenyl tetrazolium chloride or triphenyl tetrazolium hexafluorophosphate were used as controls, one solution being exposed to UV light and one not being exposed.

Samples were analysed by mass spectroscopy after exposure as described above. The irradiatied triphenyl tetrazolium control sample showed a product with a peak at m/z of 297, indicative of the sample containing the photo-product shown below:

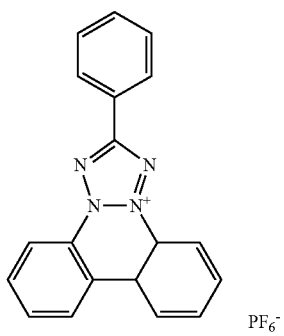

PF$_6^-$

The mass spectrum of the irradiated control sample also showed the presence of a formazan. The peak at m/z of 297 was not present in the non-irradiated sample.

No evidence of photo coupled or photo reduced products was found in the irradiated solutions of Compounds IV-VII, indicating that the compounds are stable to exposure to UV light.

COMPARATIVE EXAMPLES

Many known compounds were tested to determine their UV and base stability. The compounds below were found to be unstable when exposed to UV light and/or base.

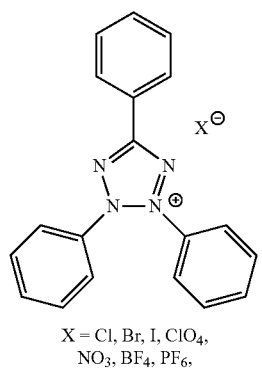

X = Cl, Br, I, ClO$_4$, NO$_3$, BF$_4$, PF$_6$,

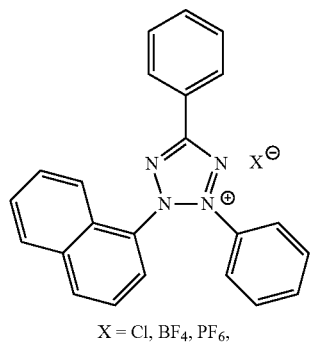

X = Cl, BF$_4$, PF$_6$,

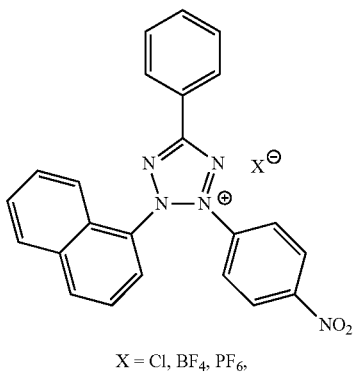

X = Cl, BF$_4$, PF$_6$,

-continued
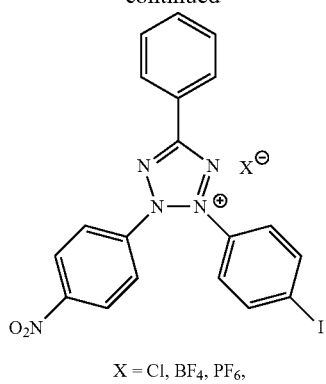
X = Cl, BF₄, PF₆,
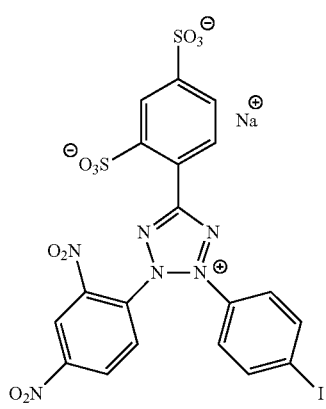
XTT
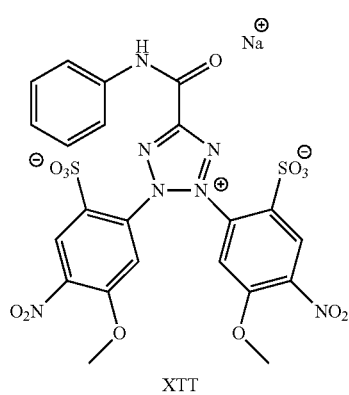
X = Br, I, ClO₄,
NO₃, BF₄, PF₆,
Thiazolyl Blue Tetrazolium
-continued
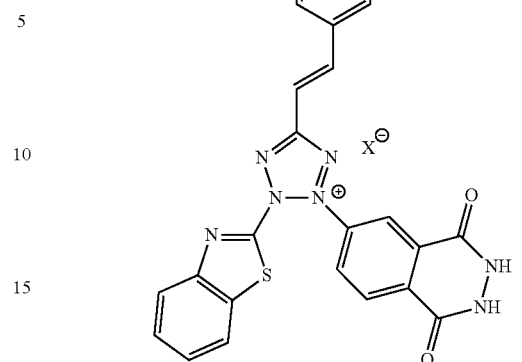
X = Cl, PF₆,
2-(2′-Benzothiazolyl)-5-styryl-
3-(4′-phthalhydrazidyl)
tetrazolium chloride
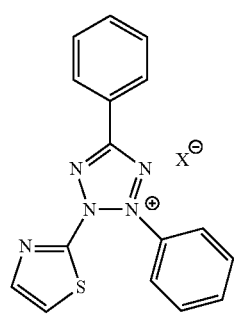
CTC (chloride form)
X = Cl, BF₄, PF₆,
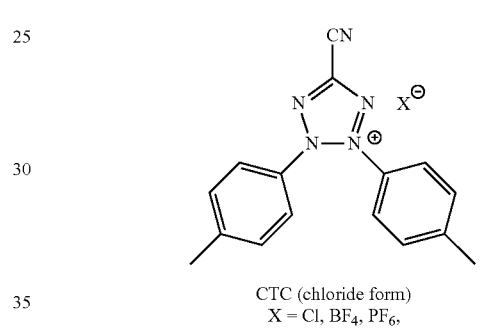
X = Cl, BF₄, PF₆,
Neotetrazolium Blue
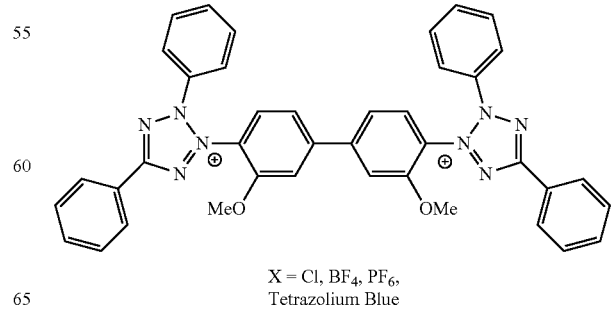
X = Cl, BF₄, PF₆,
Tetrazolium Blue -continued

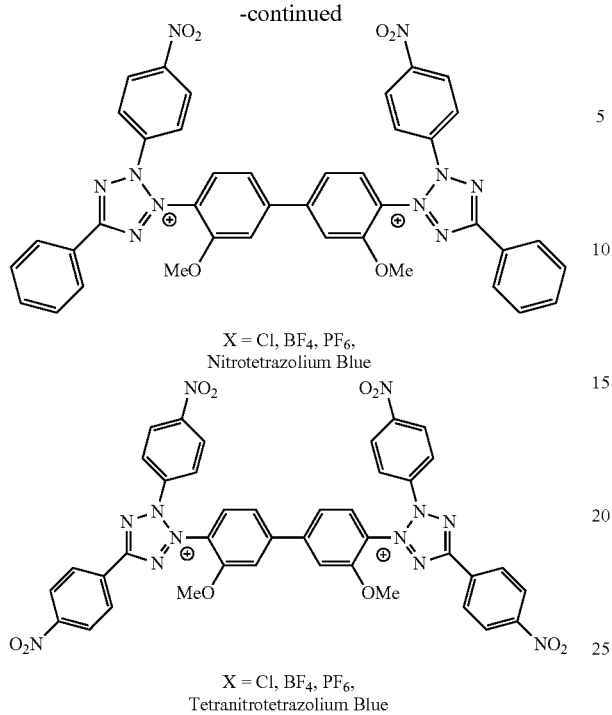

X = Cl, BF$_4$, PF$_6$,
Nitrotetrazolium Blue

X = Cl, BF$_4$, PF$_6$,
Tetranitrotetrazolium Blue

An embodiment of an example of the method of the second aspect of the present invention will now be described.

Method Example 1

A stock solution comprising 1 mMolar in compound IV and 200 mMolar in tetrabutylammonium hydroxide (TBAOH) was prepared in a 10:7 mixture of butoxyethanol and water. Known thiols (1 µL, or dissolved equivalent) were added to 200 µL of the stock solution. After a 5 second reaction period at 21° C. the sample was diluted to 3 mL with isopropyl alcohol and the electronic absorption spectrum measured. The thiols were either added as the neat compound or as a solution in a range of polar or non-polar solvents. A rapid colour change (almost instantaneous, and taking approximately 1-3 seconds) was observed with the following thiols (with cysteine giving a slower response): Ethyl mercaptan, n-butyl mercaptan, n-octyl mercaptan, benzyl mercaptan, 2-phenylethyl mercaptan, thiophenol, p-thiocresol, p-cholorothiophenol, 2-thionaphthol and cysteine.

Method Example 2

A stock solution comprising 1 mMolar in compound IV and 200 mMolar in TBAOH was prepared in a 10:7 mixture of butoxyethanol and water. Known thioesters and thiophosphorous esters (1 µL, or dissolved equivalent) were added to 200 µL of the stock solution. Each analyte was either added as a neat compound or as a solution. A rapid colour change was observed, but this was slower than for the thiols. In most cases, a change in colour was notable within a few seconds of mixing the analyte with the solution of compound IV. After a 5 minute reaction period at 21° C. the sample was diluted to 3 mL with isopropyl alcohol and the electronic absorption spectrum measured. Importantly, chemical warfare agents VX and VG provided an instant response, with the intensity of the colour increasing over a 5-10 minute period. The thioesters and thiophosphorous esters which were examined and which provided a positive response were:

Thioesters

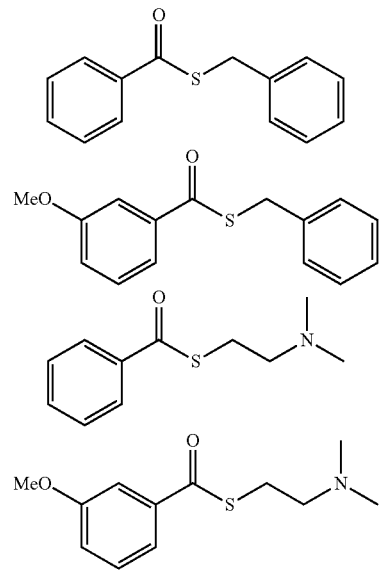

Thiophosphorous Esters

Profenofos, iprobenfos, demeton-S-methyl, demeton-S-methyl sulfone, VX and VG.

Method Example 3

A further example of an embodiment of the method of the present invention is now described using the cholinesterase inhibitor ethyl ({2-[bis(propan-2-yl)amino]ethyl}sulfanyl)(methyl)phosphinate (VX) as an analyte.

Solution A

A 5 mg/mL solution of 5-(4-tert-butylphenyl)-2-(2,6-difluorophenyl)-3-phenyl tetrazolium hexafluorophosphate chloride (the chloride salt of compound VI above) in 1:1 2-butoxyethanol/water was prepared.

Solution B

A solution comprising of a mixture of 1 mL of 40 wt. % tetrabutylammonium hydroxide in 4 mL water and 0.5 mL 2-butoxyethanol was prepared.

0.15 mL of solution A was mixed with 1.0 mL of solution B. The analyte was then added. A red colouration indicated the presence of the analyte. The speed and magnitude of the response is directly proportion to the quantity of added analyte.

Comparative Method Examples

Compounds with thiophosphoryl (P=S) groups as the sole source of sulphur (such as parathion, cyanophos and thioazin) gave a negative result.

Device Example 1

An embodiment of an example of a device in accordance with the present invention was made as follows. A solution of 0.05M Compound VI in dichloromethane was deposited onto a portion of cellulose-based filter paper. The filter paper was dried for 1 hour at 40° C. The filter paper was then immersed briefly in 0.1M sodium hydroxide solution and dried in a flow of air at room temperature.

The device of Device Example 1 was then used to detect the presence of hydrogen sulphide. The device was exposed to hydrogen sulphide and a red colouration was instantly observed. The device was also used to detect the presence of methyl mercaptan and ethyl mercaptan vapours. The colouration forms more quickly and provides a deeper colour if the paper is moistened with water or a polar organic solvent (e.g. butoxyethanol) prior to exposure to the analyte.

Further devices were made and tested using glass-microfibre (Whatman GF/A) filter paper and ion exchange filter paper (Whatman SG81).

Device Example 2

An alternative embodiment of an example of a device in accordance with the present invention was made as follows. A solution of 0.05M Compound VI in dichloromethane was deposited onto a portion of cellulose-based filter paper. The filter paper was dried for 1 hour at 40° C. In this case, the filter paper was not impregnated with base.

The device of Device Example 2 was then used to detect the presence of the liquid analytes profenofos and VX. In each case, a small amount of analyte was placed on the filter paper and the paper was then treated with a solution of 0.1M NaOH in 50% BuO($C_2H_4$)OH/water. An instant colour change was observed for both profenofos and VX. The detection limit for profenofos is estimated to be about 0.2 μL. The device gave a strong positive response with 1 μL of VX.

Further devices were made and tested using glass-microfibre (Whatman GF/A) filter paper and ion exchange filter paper (Whatman SG81).

The devices of Device Examples 1 and 2 were made and tested using compound V instead of Compound VI. Such devices produced results very similar to the devices which used Compound VI.

The reaction mixtures from Method Example 1 and the reaction mixture obtained from the thioesters of Method Example 2 were analysed using mass spectroscopy. Each reaction mixtures contained a significant amount of disulphide. Whilst not wishing to be bound by theory, the applicant believes that the presence of disulphide suggests that the reaction involves the formation of a thiolate ion which reacts with the tetrazolium compound to form a disulphide and a formazan, the formazan forming an anion at the high pHs used in the present reaction.

A proposed reaction scheme is suggested:

Whilst the method and device of the present invention have been described using the novel compounds of the present invention, those skilled in the art will realise that other tetrazolium compounds could be used.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims.

The invention claimed is:

1. A method for the detection of sulphur containing phosphorylating agents, the method comprising:
   bringing together a tetrazolium reagent, a suspected sulphur-containing phosphorylating agent and one of:
   (i) a base in aqueous alkaline conditions having a pH of at least 11; or
   (ii) a nucleophilic base in non-aqueous conditions, wherein
   the tetrazolium reagent has a structure comprising a tetrazole ring in accordance with Structure 3:

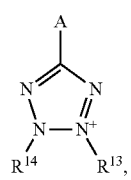

Structure 3 wherein $R^{13}$ and $R^{14}$ each comprise a phenyl moiety, wherein the phenyl moiety is optionally substituted, provided that at least one $R^{13}$ or $R^{14}$ phenyl moiety is substituted with at least two substituents, with one substituent located ortho to the tetrazole ring, and another substituent located at a second position ortho to the tetrazole ring, and
   A is a phenyl moiety, wherein A is optionally substituted, and wherein each substituent for $R^{13}$, $R^{14}$, or A is independently selected from the group consisting of halogen, $C_{1-12}$ alkyl, $-NO_2$, $-SO_3^-$, $C_{1-12}$ alkoxy and $C_{1-12}$ alkenyl.

2. The method according to claim 1, wherein the tetrazolium reagent, the suspected sulphur-containing phosphorylating agent and base are brought together in aqueous alkaline conditions wherein the pH is at least 12.

3. The method according to claim 1, wherein the suspected sulphur-containing phosphorylating agent is an agent comprising a sulphur moiety bonded with a single bond to an adjacent moiety.

4. The method according to claim 1 comprising sensing for the presence of coloration.

5. The method according to claim 1 comprising bringing together the suspected sulphur-containing phosphorylating agent, the base and tetrazolium reagent.

6. The method according to claim 1 comprising bringing together the suspected sulphur-containing phosphorylating agent and the tetrazolium reagent to form a mixture, and subsequently bringing together the base with the mixture.

7. The method according to claim 1 comprising bringing together the suspected sulphur-containing phosphorylating agent and the base to form a mixture, and subsequently bringing together the tetrazolium reagent with the mixture.

8. The method according to claim 1 comprising providing a device for detecting the presence of a sulphur-containing phosphorylating agent, the device comprising a substrate provided with the tetrazolium reagent.

9. A The method according to claim 8 wherein the substrate is provided with base and the method comprises contacting the substrate with the suspected sulphur-containing phosphorylating agent.

10. The method according to claim 1 comprising providing a kit for detecting the presence of a sulphur-containing phosphorylating agent, the kit comprising a substrate optionally provided with the tetrazolium reagent and/or base, and, if the substrate is not provided with the tetrazolium reagent or base, then the kits further being provided with one or more of a basic solution, a solution of tetrazolium reagent and a sample collector.

11. The method according to claim 10 wherein the kit comprises a sample collector and the sample collector comprises (i) a surface for the collection of a sample, the surface being provided by an absorbent material or porous material, or (ii) a chamber for holding a sample and a means for urging a sample into the chamber.

12. The method according to claim 1, wherein the tetrazolium reagent, the suspected sulphur-containing phosphorylating agent and base are brought together in aqueous alkaline conditions wherein the pH is at least 13.

* * * * *